(12) United States Patent
Guo et al.

(10) Patent No.: US 8,603,750 B2
(45) Date of Patent: Dec. 10, 2013

(54) METHODS FOR ASSAYING ANALYTES USING PHOTOELECTROCHEMICAL LABELS

(75) Inventors: Lianghong Guo, Beijing (CN); Dong Dong, Beijing (CN); Dong Zheng, Beijing (CN); Fuquan Wang, Beijing (CN); Xiqiang Yang, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1552 days.

(21) Appl. No.: 10/535,905

(22) PCT Filed: May 6, 2003

(86) PCT No.: PCT/CN03/00327
§ 371 (c)(1), (2), (4) Date: Nov. 25, 2005

(87) PCT Pub. No.: WO2004/046721
PCT Pub. Date: Jun. 3, 2004

(65) Prior Publication Data
US 2006/0148102 A1    Jul. 6, 2006

(30) Foreign Application Priority Data
Nov. 21, 2002 (CN) .................................. 02 1 48800

(51) Int. Cl.
*G01N 33/53* (2006.01)
*G01N 21/76* (2006.01)

(52) U.S. Cl.
USPC .......................................... 435/7.1; 436/172

(58) Field of Classification Search
USPC ................ 436/546, 172, 84; 435/7.1, 6, 7.92, 435/7.93; 546/256
See application file for complete search history.

(56) References Cited

U.S. PATENT DOCUMENTS

| | | | |
|---|---|---|---|
| 4,293,310 A | 10/1981 | Weber | |
| 4,927,721 A | 5/1990 | Gratzel et al. | |
| 5,714,089 A * | 2/1998 | Bard et al. | 252/301.18 |
| 6,066,448 A | 5/2000 | Wohlstadter et al. | |
| 6,140,138 A | 10/2000 | Bard et al. | |
| 7,314,711 B2 * | 1/2008 | Richter et al. | 435/6 |

FOREIGN PATENT DOCUMENTS

| | | |
|---|---|---|
| CN | 1249815 | 4/2000 |
| CN | 1325490 | 12/2001 |
| JP | 1-220380 | 9/1989 |
| JP | 2000-323190 | 11/2000 |
| JP | 2002-181777 | 6/2002 |
| WO | WO-2004/046369 | 6/2004 |

OTHER PUBLICATIONS

Furst et al. Hydrazine as a reducing agent for organic compounds (catalytic hydrazine reductions). Chem. Rev., 1965, vol. 65, No. 1, pp. 51-68.*
International Search Report for PCT/CN03/00327, mailed on Aug. 21, 2003, 4 pages.
Weber et al., Clin. Chem. (1983) 29:1665-1672.
Dong et al., Analytical Chemistry (2004) 76(2):499-501.
Nakamura et al., Analytical Sciences (Supplement) (2001) 17:1431-1432.
Supplementary European Search Report for EP 03732170.0, mailed on Feb. 19, 2007, 5 pages.
Kon et al., Japan Chemical Society Abstracts of Annual Meeting (2001) 79(1):8.
Nakamura et al., Japan Chemical Society Abstracts of Annual Meeting (2002) 81(2):947.
Notice of Final Rejection from Japanese Patent Application No. 2004-552345, mailed on Jan. 12, 2010.

* cited by examiner

*Primary Examiner* — Shafiqul Haq
(74) *Attorney, Agent, or Firm* — Morrison & Foerster LLP

(57) ABSTRACT

The present invention provides apparatus, kits and methods for assaying analytes using photoelectrochemical molecules as labels. Specifically, the present invention provides a method for assaying an analyte, comprising: a) contacting a sample suspected of containing an analyte with a reactant capable of binding and/or reacting with the analyte under suitable conditions to allow binding of analyte, if present in the sample, to the reactant; and b) assessing binding and/or reacting between the analyte and the reactant to determine presence and/or amount of analyte in the sample, wherein the reactant, analyte, or additional reactant or additional analyte or analyte analog is labeled with a photoelectrochemically active molecule. The assessing step also comprises converting the photoelectrochemically active molecule with light to an excited state in the presence of an electrode, and assessing an electric current generated by an electron transfer between the excited photoelectrochemically active molecule and the electrode.

34 Claims, 3 Drawing Sheets

METHODS FOR ASSAYING ANALYTES USING PHOTOELECTROCHEMICAL LABELS

CROSS-REFERENCE TO RELATED APPLICATIONS

This application is the national phase of PCT application PCT/CN2003/000327 having an international filing date of May 6, 2003, which claims priority from China application number 02148800.2 filed Nov. 21, 2002. The contents of these documents are incorporated herein by reference.

TECHNICAL FIELD

The present invention relates to apparatuses and methods for assaying analytes. More particularly, the present invention relates to apparatuses and methods for assaying analytes using photoelectrochemical labels.

BACKGROUND ART

A continuous and expanding need exists for rapid, highly specific methods of detecting and quantifying chemical, biochemical, and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, metabolites, enzymes and nucleic acids.

The presence of these materials can often be determined by binding methods which exploit the high degree of specificity which characterizes many biochemical and biological systems. Frequently used methods are based on, for example, antigen-antibody systems, nucleic acid hybridization techniques, and protein-ligand systems. In these methods, the existence of the complex of diagnostic value is typically indicated by the presence or absence of an observable label which has been attached to one or more of the complexing materials.

The specific labeling method chosen often dictates the usefulness and versatility of a particular system for detecting a material of interest. A label is preferably inexpensive, safe, and capable of being attached efficiently to a wide variety of chemical, biochemical, and biological materials without changing the important binding characteristics of those materials. Moreover, the label is preferably stable, and gives a highly characteristic signal. Detection of the label is preferably rapid, sensitive, and reproducible without the need for expensive, specialized facilities or personnel. Quantification of the label is preferably relatively independent of variables such as temperature and the composition of the mixture to be assayed.

A wide variety of labels have been developed, each with particular advantages and disadvantages. For example, radioactive labels are versatile, and can be detected at very low concentrations, However, they are expensive, hazardous, and their use requires sophisticated equipment and trained personnel. Moreover, radioactive labels cannot be used in homogeneous methods. Disposal of radioactive waste is also of increasing concern both because of the potential risk to the public and the lack of radioactive waste disposal sites. The use of radioactive labeling is also time consuming, and can sometimes require as much as several days for detection of the radioactive label.

Enzyme labels and absorption-based detection instrument, e.g., ELISA, are safe, but lack sensitivity and stability for long term storage. Moreover, in enzyme immunoassay such as ELISA, a number of analysis steps are involved and a long period of time is required for the reaction. Fluorescent organic and inorganic molecules are safe and stable, but do not provide the same sensitivity as radio-isotope labels. With laser as an excitation source and complex optical detection, instrument cost is also a major disadvantage for fluorescent labels. Chemiluminescence and electrochemiluminescence provide high sensitivity for detection, but also employ optical detection and have relatively high instrument cost.

Photoelectrochemical labels for immunoassays have previously been described. For example, U.S. Pat. No. 4,293,310 describes an apparatus and method comprising a quencher and an electrochemical flow cell with a light means for determining the presence of photoelectrochemically labeled materials. Upon photoexcitation, the photoelectrochemically active label transfers an electron to a quencher molecule. The oxidized molecule is subsequently reduced with an electron from an electrode of the flow cell which is held at suitable potential. This electron is measured as photocurrent. The amount of free labeled analyte in the system is determined by the photocurrent signal. Although photoelectrochemical detection methods are cheaper than imaging devices employed in luminescence-based detection methods, this method has a limited detection range, and also suffers from interferents. (See Weber et al., *Clin. Chem.*, 29:1665-1672 (1983)). Thus, there remains a need for analytical compositions and methods that are safe, stable, efficient, and inexpensive, and that provide a wide detection range.

DISCLOSURE OF THE INVENTION

The present invention provides methods for assaying analytes using photoelectrochemical molecules as labels. The application of photoelectrochemistry in analytical methods have several advantages. First, the excitation source and detection signal are separate physical parameters, resulting in a minimal background interference from the excitation source. Second, the photoelectrochemical process is initiated by light and can easily be controlled by turning a light source on or off, unlike chemilumiscence. When the light is off, there is no photoelectrochemical reaction. Third, the excitation source for the photoelectrochemical process does not have to be a monochromic light, unlike fluorescence. Fourth, electronic detection for a photoelectrochemical process is cheaper than the imaging devices employed in luminescence-based detection such as fluorescence, chemiluminescence and electrochemiluminescence. The combination of white-light excitation and electronic detection greatly reduces instrument cost. The present invention also provides superior results compared to other photoelectrochemical assays where the species generating the photocurrent is an oxidized, ground state labeling molecule.

In one embodiment, the present invention provides a method for assaying an analyte, which method comprises: a) contacting a sample suspected of containing an analyte with a reactant capable of binding and/or reacting with said analyte under suitable conditions to allow binding of said analyte, if present in said sample, to said reactant; and b) assessing binding and/or reacting between said analyte and said reactant to determine presence and/or amount of said analyte in said sample, wherein said reactant, said analyte, or additional reactant or additional analyte or analyte analog is labeled with a photoelectrochemically active molecule and said assessing in step b) comprises converting said photoelectrochemically active molecule with light to an excited state in the presence of an electrode and assessing an electric current generated by an electron transfer between said excited photoelectrochemically active molecule and said electrode.

The analyte can be any biological analyte, such as a cell, a cellular organelle, a virus, an aggregate or complex thereof. The cell can be any cell such as an animal cell, a plant cell, a fungus cell, a bacterium cell, a recombinant cell, or a cultured cell. The cellular organelle can be any cellular organelle such as a nuclei, a mitochondrion, a chloroplast, a ribosome, an endoplasmic reticulum, a Golgi apparatus, a lysosome, a proteasome, a secretory vesicle, a vacuole, or a microsome. The analyte can also be a hormone, a cancer marker, a steroid, a sterol, a pharmaceutical compound, a metabolite of a pharmaceutical compound, or a complex thereof.

The analyte can also be any chemical analyte, such as a molecule, an inorganic molecule, an organic molecule, or a complex thereof. The organic molecule can be an amino acid, a peptide, a protein, a nucleoside, a nucleotide, an oligonucleotide, a nucleic acid, a vitamin, a monosaccharide, an oligosaccharide, a carbohydrate, a lipid, or a complex thereof.

In one embodiment, the sample is a mammalian sample. The mammal can be a bovine, goat, sheep, equine, rabbit, guinea pig, murine, human, feline, monkey, dog, or porcine. The sample can also be a clinical sample, such as serum, plasma, whole blood, sputum, cerebral spinal fluid, amniotic fluid, urine, gastrointestinal contents, hair, saliva, sweat, gum scrapings, or biopsy tissue. The clinical sample can be a human clinical sample. In another embodiment, the sample is a body fluid sample.

Preferably, the reactant binds and/or reacts specifically with the analyte. Non-limiting examples of reactants include cells, cellular organelles, virus, molecules, and an aggregate or complex thereof. In one embodiment, the reactant is an antibody. In another embodiment, the reactant is a nucleic acid.

The reactant or the analyte can be labeled with a photoelectrochemically active molecule. In one embodiment, the photoelectrochemically active molecule is a metal polypyridyl complex. Alternatively, the photoelectrochemically active molecule has the formula,

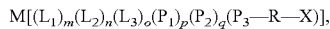

wherein M is a metal ion, $L_1, L_2, L_3$ are mono-dentate ligands of M, $P_1, P_2, P_3$ are poly-dentate ligands of M, R is a spacer, X is a reactive chemical group capable of linking the photoelectrochemically active molecule to another moiety, e.g., a reactant or an analyte, m, n, o, p and q are either zero or a positive integer, and total number of bonds provided by all the ligands equal to the coordination number of M.

Any suitable metal ions can be sued. For example, the metal ion can be osmium, ruthenium, zinc, magnesium, or aluminum. The $L_1$, $L_2$ or $L_3$ moiety can be the same or different. In one embodiment, the $L_1$, $L_2$, $L_3$ is a cyanide or a thiocyanide. In another embodiment, the R group is a $C_{2-12}$ alkyl or poly(ethylene glycol). In still another embodiment, the X group is N-hydroxysuccinimide ester, a sulfhydryl, an epoxide, an aldehyde, a maleic anhydride, an imidoester, an amino, a carboxyl, an iosthiocyanate, a maleimide, a haloacetyl, a hydrazide and a phosphoramidite.

The $P_1$, $P_2$ or $P_3$ moiety can be a nitrogen-containing aromatic heterocycle. Non-limiting examples of the nitrogen-containing aromatic heterocycle are bipyridyl, bypyrazyl, terpyridyl, phenanthrolyl, or phthalocyanine. The bipyridyl, bypyrazyl, terpyridyl, phenanthrolyl or phthalocyanine groups can be unsubstituted or substituted. Non-limiting examples of substituted groups include an alkyl, an aryl, an aralkyl, a carboxylate, a carboxyaldehyde, a carboxamide, a cyano, an amino, a hydroxycarbonyl, a hydroxyamino, an aminocarbonyl, an amidine, a guanidium, an ureide, a sulfur-containing group, a phosphorous-containing group, and a carboxylate ester of N-hydroxysuccinimide.

The present methods can be conducted in any suitable assay format. For example, the present methods can be conducted in a competition assay format. In a competition assay, the reactant and the analyte from the sample are not labeled, and a separate analyte or analyte analog labeled with a photoelectrochemically active molecule is used. The present methods can also be conducted in a sandwich assay format. In a sandwich assay format, a first reactant and the analyte from the sample are not labeled, and a second reactant labeled with a photoelectrochemically active molecule is used.

In one embodiment, the binding or reacting between the analyte and the reactant is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, chemiluminescence assay, lateral flow immunoassay, μ-capture assay, inhibition assay, energy transfer assay, avidity assay, turbidometric immunoassay, or time resolved amplified cryptate emission (TRACE) assay.

In another embodiment, the assessing step further comprises converting the photoelectrochemically active molecule with light to an excited state in the presence of an electrode and a regenerating (either reducing or oxidizing) agent, and assessing an electric current generated by an electron transfer between the excited photoelectrochemically active molecule and the electrode, and the oxidized or reduced photoelectrochemically active molecule at a ground state resulted from the electron transfer is reduced or oxidized by the regenerating agent to a reduced or oxidized photoelectrochemically active molecule at a ground state that can be again excited with light. Any suitable regenerating agent can be used in the present methods. For example, the regenerating agent can be a hydroquinone solution.

The present invention also provides kits for assaying an analyte. In one embodiment, the kit comprises: a) a reactant capable of binding and/or reacting with an analyte under suitable conditions to allow binding of said analyte, if present in a sample, to said reactant; and b) means for assessing binding and/or reacting between said analyte and said reactant to determine presence and/or amount of said analyte in said sample, wherein said reactant, said analyte, or additional reactant or additional analyte or analyte analog is labeled with a photoelectrochemically active molecule and said assessing in step b) comprises converting said photoelectrochemically active molecule with light to an excited state in the presence of an electrode and assessing an electric current generated by an electron transfer between said excited photoelectrochemically active molecule and said electrode.

The kit can further comprise a regenerating agent to reduce or oxidize the oxidized or reduced photoelectrochemically active molecule at a ground state resulted from the electron transfer to a reduced or oxidized photoelectrochemically active molecule at a ground state that can be excited again with light. The kit can also comprise an instruction for using the kit to assay the analyte.

Furthermore, the present invention provides an apparatus for assaying an analyte. In one embodiment, the apparatus comprises: a) a reactant capable of binding and/or reacting with an analyte under suitable conditions to allow binding of said analyte, if present in a sample, to said reactant; b) a photoelectrochemically active molecule attached to a reactant, an analyte or an analyte analog; c) an electrode suitable for assessing an electric current generated by an electron transfer between an excited photoelectrochemically active molecule and said electrode; d) a regenerating agent to convert oxidized or reduced photoelectrochemically active to a ground state that can be again excited with light; e) an electrochemical-cell having a wall transparent to light of a spectrum which will excite said photoelectrochemically active molecule; and f) light means which further comprise a light source having a spectrum capable of exciting said photoelectrochemically active molecule, and means for isolating said spectrum if necessary, wherein the energy level of said electrode, the redox potential of said regenerating agent and the distance from said photoelectrochemically active molecule to said electrode are adjusted to ensure measurement of an electric current generated by an electron transfer between said excited photoelectrochemically active molecule and said electrode.

Any suitable light source can be used. For example, the light source can be a hollow cathode lamp, a Xe arc lamp, a Xe—Hg lamp, a metal halide lamp, a light-emitting diode, or a laser.

The apparatus can further comprise a means for distinguishing the electron transfer between the excited photoelectrochemically active molecule and the electrode from other electron transfer(s). The means for distinguishing the electron transfer between the excited photoelectrochemically active molecule and the electrode from other electron transfer(s) can further comprise a light beam chopper, filters, lenses, or a lock-in amplifier. The means for distinguishing the electron transfer between the excited photoelectrochemically active molecule and the electrode from other electron transfer(s) can also further comprise a first working electrode exposed to light and a second working electrode in the dark, such that the difference in current signals is the signal due to the presence of light.

In one embodiment, the means for isolating the spectrum further comprises a monochromater. In another embodiment, the means for isolating the spectrum further comprises an optic filter. The isolated spectrum can have a range between 400 nm and 800 nm.

MODES OF CARRYING OUT THE INVENTION

Figure 1:
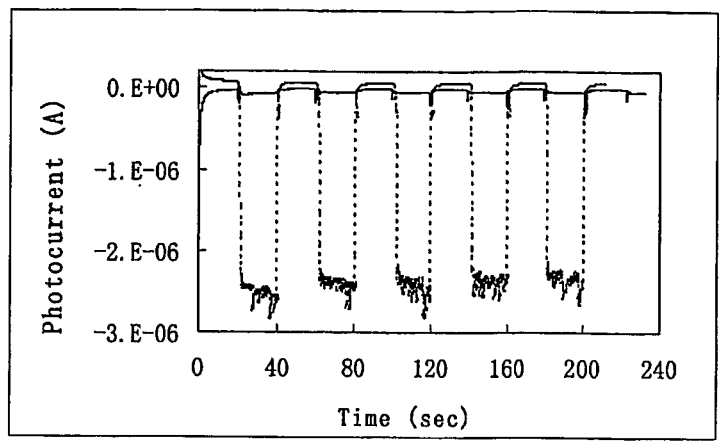
FIG. 1 illustrates photocurrent of ruthenium tris(4,4'-dicarboxyl-2,2'-bipyridine) adsorbed on $TiO_2$ film electrode.

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "photoelectrochemically active molecule" refers to a molecule which when in solution produces an electrical current at an electrode in response to the input of light to the solution.

As used herein, "photocurrent" refers to the electrical current produced by a photoelectrochemically active molecule.

As used herein, "ligand" refers to any ion, molecule, molecular group, or other substance that binds to another entity to form a larger complex. Examples of ligands include, but are not limited to, peptides, carbohydrates, nucleic acids, e.g., DNA and RNA, antibodies, or any molecules that bind to receptors.

As used herein, "mono-dentate ligand" refers to a ligand having one moiety for binding to another entity.

As used herein, "polydentate ligand" refers to a ligand having more than one moiety for binding to another entity.

As used herein, "label" refers to any atom, molecule or moiety which can be used to provide a detectable signal.

As used herein, "antibody" refers to specific types of immunoglobulin, i.e., IgA, IgD, IgE, IgG, e.g., $IgG_1$, $IgG_2$, $IgG_3$, and $IgG_4$, and IgM. An antibody can exist in any suitable form and also encompass any suitable fragments or derivatives. Exemplary antibodies include a polyclonal antibody, a monoclonal antibody, a Fab fragment, a Fab' fragment, a $F(ab')_2$ fragment, a Fv fragment, a diabody, a single-chain antibody and a multi-specific antibody formed from antibody fragments.

As used herein, "nucleic acid" refers to any nucleic acid containing molecule including, but not limited to DNA, RNA or PNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth, and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" and "bacterium" refer to all prokaryotic organisms, including those within all of the phyla in the Kingdom Procaryotae. The term encompass all microorganisms considered to be bacteria including *Mycoplasma, Chiamydia, Actinomyces, Streptomyces,* and *Rickettsia*. All forms of bacteria are included within this definition, including cocci, bacilli, spirochetes, spheroplasts, protoplasts, etc.

As used herein, "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat. Some virions also have a lipid containing membrane. The term "virus" encompasses all types of viruses, including animal, plant, phage, and other viruses.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "sample" refers to anything which may contain an analyte to be assayed using the present methods and/or devices. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Biological tissues may be processed to obtain cell suspension samples. The sample may also be a mixture of cells prepared in vitro. The sample may also be a cultured cell suspension. In case of the biological samples, the sample may be crude samples or processed samples that are obtained after various processing or preparation on the original samples. For example, various cell separation methods (e.g., magnetically activated cell sorting) may be applied to separate or enrich target cells from a body fluid sample such as blood. Samples used for the present invention include such target-cell enriched cell preparation.

As used herein, "analyte" refers to any material that is to be analyzed. Such materials include, but are not limited to, ions, molecules, antigens, bacteria, compounds, viruses, cells, antibodies, and cell parts, etc.

As used herein, "antigen" refers to any molecule or molecular group that is recognized by at least one antibody. By definition, an antigen contains an epitope (i.e., the specific biochemical unit capable of being recognized by the antibody). The term "immunogen" refers to any molecule, compound, or aggregate that induces the production of antibodies. By definition, an immunogen contains an epitope (i.e., the specific biochemical unit capable of causing an immune response).

As used herein, "specific binding" refers to the binding of one material to another in a manner dependent upon the presence of a particular molecular structure. For example, a receptor will selectively bind ligands that contain the chemical structures complementary to the ligand binding site(s). In contrast, "non-specific binding" refers to interactions that are arbitrary and not based on structural compatibilities of the molecules.

As used herein, "specific binding pair" refers to any substance, or class of substances, which has a specific binding affinity for the ligand to the exclusion of other substances. In one embodiment, the specific binding pair includes specific binding assay reagents which interact with the sample ligand or the binding capacity of the sample for the ligand in an immunochemical manner. For example, there will be an antigen-antibody or hapten-antibody relationship between reagents and/or the sample ligand or the binding capacity of the sample for the ligand. Additionally, it is well understood in the art that other binding interactions between the ligand and the binding partner serve as the basis of specific binding assays, including the binding interactions between hormones, vitamins, metabolites, and pharmacological agents, and their respective receptors and binding substances. (See e.g., Langan et al. (eds.), Ligand Assay, pp. 211 et seq., Masson Publishing USA Inc., New York, 1981).

As used herein, "plasma" refers to the fluid, noncellular portion of the blood, distinguished from the serum obtained after coagulation.

As used herein, "serum" refers to the fluid portion of the blood obtained after removal of the fibrin clot and blood cells, distinguished from the plasma in circulating blood.

As used herein, "fluid" refers to any composition that can flow. Fluids thus encompass compositions that are in the form of semi-solids, pastes, solutions, aqueous mixtures, gels, lotions, creams, and other such compositions.

As used herein, "alkyl" encompasses straight or branched alkyl groups, including alkyl groups that are optionally substituted with one or more substituents. For example, the alkyl group can be optionally substituted with hydroxy, halogen, aryl, alkoxy, acyl, or other substituents known in the art. One of more carbon atoms of the alkyl group can also be optionally replaced by one or more heteroatoms.

As used herein, "substitute" refers to the replacement of a hydrogen atom in a compound with a substituent group.

As used herein, "electrode" refers to an electric conductor or semiconductor through which an electric current enters or leaves a medium. The medium can be an electrolytic solution, a solid, molten mass, gas or vacuum.

As used herein, "electrochemical flow cell" or "electrochemical cell" refers to a combination of two or more electrodes arranged so that an overall oxidation-reduction reaction produces an electromotive force. Non-limiting examples include dry cells, wet cells, standard cells, fuel cells, solid-electrolyte cells, and reserve cells.

As used herein, "reducing agent" refers to any reagent that removes oxygen, contributes hydrogen, or contributes electrons. The reducing agent is oxidized in the reduction process. The relative strengths of reducing agents can be inferred from their standard electrode potentials. By convention, the standard electrode potentials are reduction potentials, or the tendency to be reduced. Thus, the strongest reducing agents will have large negative electrode potentials. (See e.g., Bard and Faulkner, Electrochemical Methods, Wiley, New York, 1980).

As used herein, "oxidizing agent" refers to any agent that contributes oxygen, extracts hydrogen, or extracts electrons. The oxidizing agent is reduced in the oxidation process. The relative strengths of oxidizing agents can be inferred from their standard electrode potentials. By convention, the strongest oxidizing agent will have large positive electrode potentials. (See e.g., Bard and Faulkner, Electrochemical Methods, Wiley, New York, 1980).

B. METHODS FOR ASSAYING ANALYTES USING PHOTOELECTROCHEMISTRY

The present invention provides methods for assaying analytes using photoelectrochemistry. The present invention can be used for the detection of chemical and biological affinity reactions and analytes, but is not limited to detection of particular reactions or analytes.

Photoelectrochemistry (PEC) refers to the phenomenon of electrochemistry initiated by light excitation. PEC may have different formats. In one example, when a photoelectrochemically active molecule is irradiated with light, electrons in the ground state absorb the light energy and migrate from the ground state L(G) to the excited state L(E) (Eq. 1). The excited electron is more reactive, and may be easily lost. For example, the excited electron may move from the excited molecule to a semiconducting electrode having a lower energy level, generating a photocurrent (Eq. 2). Once the excited electron leaves the molecule, it becomes oxidized L(O). If a reducing agent exists in solution, the molecule can convert back to its original state, and participate in the photoelectrochemical reaction again (Eq. 3). Thus, the photocurrent is sustained.

$$\text{Photo-excitation: } L(G) + h\nu \rightarrow L(E) \quad \text{(Eq. 1)}$$

$$\text{Photo-current: } L(E) \rightarrow (O) + e(\text{electrode}) \quad \text{(Eq. 2)}$$

$$\text{Regeneration: } L(O) + \text{Reducing Agent} \rightarrow L(G) \quad \text{(Eq. 3)}$$

In one aspect, the present invention provides a method for assaying an analyte, comprising: a) contacting a sample suspected of containing an analyte with a reactant capable of binding and/or reacting with the analyte under suitable conditions to allow binding of analyte, if present in the sample, to the reactant; and b) assessing binding and/or reacting between the analyte and the reactant to determine presence and/or amount of analyte in the sample. Specifically, the reactant, analyte, or additional reactant or additional analyte or analyte analog is labeled with a photoelectrochemically active molecule. The assessing step also comprises converting said photoelectrochemically active molecule with light to an excited state in the presence of an electrode and assessing an electric current generated by an electron transfer between said excited photoelectrochemically active molecule and said electrode.

In one embodiment, one member of a specific binding pair is immobilized as the capture reagent on an electrode surface. The other specific binding pair member is labeled with a photoelectrochemically active molecule. After sample addition and specific binding reaction, the photoelectrochemically labeled molecule would accumulate on the electrode surface in an amount related to the concentration of the analyte. To detect the reaction, a beam of light is directed at the electrode in contact with a liquid containing a reducing agent, and the resulting photocurrent is measured.

The present invention can also be used in a sandwich immunoassay. For example, the primary antibody is immobilized on an electrode as a capture antibody for photocurrent detection. The secondary antibody is labeled with a photoelectrochemically active molecule. The electrode and secondary antibody are contacted with a sample containing the antigen to be detected. After completion of the immunological reaction on the electrode surface, the electrode is contacted with a solution containing a reducing agent. A light beam is directed at the electrode, and the resulting photocurrent is measured with an electronic device.

Preferably, the reactant and analyte or analyte analog are members of a specific binding pair. Any specific binding pairs known in the art can be used to practice the present invention. Non-limiting examples of specific binding pairs include antigens and antibodies thereto; haptens and antibodies thereto; guest and host binding pairs; DNA and DNA binding pairs; DNA and oligonucleotide binding pairs; DNA and RNA binding pairs; and ligand and receptor binding pairs. Non-limiting examples of ligand and receptor binding pair include peptides, proteins, carbohydrates, glycoproteins, steroid, hormones, vitamins, metabolites, pharmacological agents, or other organic molecule and their receptors and binding substances.

Any photoelectrochemically ("PEC") active labels known in the art can be used in the present invention. The PEC active labels preferably have the following characteristics. First, the PEC label has a strong absorption in the visible region. Second, the energy level of the excited state of the PEC label is higher than that of the electrode so electron transfer can occur. Third, the excited state of the PEC label has a lifetime long enough for electron transfer to prevail over luminescence. Finally, the reduced and oxidized forms of the PEC label are stable.

Non-limiting examples of PEC labels include organic dyes, metal porphyrins, metal phthalocyanines, and metal polypyridines. Preferably, the PEC label is a metal polypyridyl complex. Non-limiting examples of metals include magnesium, aluminum, or a transition metal such as osmium, ruthenium or zinc. Non-limiting examples of transition metal complexes are ruthenium tris bipyridyl cations, ligand substituted ruthenium bipyridyl cations such as $Ru(bipyridyl)_2(NCS)_2$, or other corresponding complexes in which the bipyridyl moiety is replaced by a substituted bipyridyl derivative such as 4,4'-dicarboxyl-2,2'-bypyridyl, a bypyrazyl derivative, a terpyridyl derivative, a phenanthroline derivative, and other derivatives.

In one embodiment, the photoelectrochemical label has a formula:

$$M[(L_1)_m(L_2)_n(L_3)_o(P_1)_p(P_2)_q(P_3-R-X)],$$

wherein M is a metal ion, $L_1$, $L_2$, $L_3$ are mono-dentate ligands of M, $P_1$, $P_2$, $P_3$ are poly-dentate ligands of M, R is a spacer, X is a reactive chemical group capable of linking the photoelectrochemically active molecule to a moiety such as a reactant or an analyte, m, n, o, p and q are either zero or a positive integer, and total number of bonds provided by all the ligands equal to the coordination number of M.

The composition of the complex is such that, upon light excitation, photocurrent is produced. The metal coordinating complex M is preferably osmium or ruthenium. The monodentate ligands are preferably cyanides or thiocyanides. The poly-dentate ligands are preferably nitrogen-containing aromatic heterocyclic such as bipyridyl, bypyrazyl, terpyridyl, and phenanthrolyl, which can optionally be substituted. The substituents can be an alkyl, an aryl, an aralkyl, a carboxylate, a carboxyaldehyde, a carboxamide, a cyano, an amino, a hydroxycarbonyl, a hydroxyamino, an aminocarbonyl, an amidine, an guanidium, an ureide, a sulfur-containing group, a phosphorous-containing group and a carboxylate ester of N-hydroxysuccinimide.

The X group is preferably N-hydroxysuccinimide ester, a sulfhydryl, an epoxide, an aldehyde, a maleic anhydride, an imidoester, an amino, a carboxyl, an iosthiocyanate, a maleimide, a haloacetyl, a hydrazide and a phosphoramidite. The R group is preferably a $C_2$-$C_{12}$ alkyl chain, or a poly(ethylene glycol) chain, which can optionally be substituted with other substituents. These substituents can be halogen, hydroxy, alkoxy, nitro, cyano, carboxylic acid, alkyl, alkenyl, cycloalkyl, thiol, amino, acyl, carboxylate, aryl, carbamate, carboxamide, sulfonamide, a heterocyclic group, or any appropriate substituent known in the art.

Any electrode known in the art can be used in the present invention. For example, any electrode for use in photoelectrochemical solar cells can be used in the present invention. Any semiconductor materials capable of producing an electric current can also be used. Non-limiting examples include narrow-band semiconductor electrodes and wide-band semiconductor electrodes. The electrode can be either pure or doped semiconductor. Furthermore, it can be composed of one semiconductor or a mixture of multiple semiconductors. In one embodiment, the electrode material comprises a film of mono-dispersed, nano-crystalline $TiO_2$ on a conductive glass.

Any known oxidizing or reducing agent can be used in the present invention. The relative strength of oxidizing or reducing agents can be inferred from their standard electron potentials. In one embodiment, the reducing agent comprises hydroquinone in an aqueous electrolyte.

The present invention can be used to detect biological and chemical analytes. Non-limiting examples include cells; cellular organelles; virus; molecules; hormones such as insulin, chorionic gonadotropin, thyroxine, triiodothyronine, folliclestimulating hormone, leutinizing hormone, thyroid-stimulating hormone, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5'-adenosine monophosphate and 3',5'-guanosine monophosphate; pharmacological agents or drugs such as aminoglycoside antibiotics like gentamicin, amikacin and sisomicin, or drugs of abuse such as the opium alkaloids and ergot derivatives; antibodies such as microsomal antibody and antibodies to hepatitis and allergens; and specific binding receptors such as thyroxine binding globulin, avidin, intrinsic factor, and transcobalamin.

C. APPARATUSES AND KITS FOR ASSAYING ANALYTES USING PHOTOCHEMISTRY

The present invention also provides an analytical apparatus for assaying analytes using photoelectrochemistry. Specifically, the apparatus of the present invention comprises: a) a reactant capable of binding and/or reacting with an analyte under suitable conditions to allow binding of said analyte, if present in a sample, to said reactant; b) a photoelectrochemically active molecule attached to a reactant, an analyte or an analyte analog; c) an electrode suitable for assessing an electric current generated by an electron transfer between an excited photoelectrochemically active molecule and said electrode; d) a regenerating agent to convert oxidized or reduced photoelectrochemically active to a ground state that can be again excited with light; e) an electrochemical-cell having a wall transparent to light of a spectrum which will excite said photoelectrochemically active molecule; and f) light means which further comprise a light source having a spectrum capable of exciting said photoelectrochemically active molecule, and means for isolating said spectrum if necessary, wherein the energy level of said electrode, the redox potential of said regenerating agent and the distance from said photoelectrochemically active molecule to said electrode are adjusted to ensure measurement of an electric current generated by an electron transfer between said excited photoelectrochemically active molecule and said electrode.

Preferably, the reactant and analyte or analyte analog are members of a specific binding pair. Any specific binding pairs known in the art, as previously described above, can be used in the apparatus. Any photoelectrochemically active labels known in the art, as previously described above, can be used in the apparatus. Any electrode known in the art, as previously described above, can be used in the apparatus.

Any electrochemical flow cell with a standard set of electrodes known in the art can be used in the apparatus. (See e.g., U.S. Pat. No. 4,293,310). In one embodiment, the cell has a wall which is transparent to light having a wavelength that can excite the photoelectrochemically active species. The distance from the photoelectrochemically active molecule to the electrode is preferably adjusted to ensure measurement of an electric current generated by an electron transfer from the excited photoelectrochemically active molecule to the electrode.

The light means source can be a laser, such as an argon ion laser of dye laser. In one embodiment, the laser is suitable for exciting a ruthenium species. Other light means source include a hollow cathode lamp, a Xe lamp, a Xe—Hg lamp, a metal halide lamp, or a light-emitting diode. In one embodiment, the light means is capable of exciting a photoelectrochemically active molecule, and preferably has a spectrum range of between 400 to 800 nm. The light means can also comprise a means for isolating the spectrum if necessary, such as a monochromater or an optic filter.

In one embodiment, the apparatus of the present invention further comprises a means for distinguishing between the electron transfer from the excited photoelectrochemically active molecule to the electrode and other electron transfers. For example, the means of discriminating can distinguish between electrochemical signals which are caused by the light, and signals not caused by the light. In one embodiment, one of the electrodes is as an auxiliary electrode, one is a working electrode kept in the dark and one is a working electrode in the light. The difference in the current signals of the latter two electrodes is taken as the signal due to the presence of light. Alternatively, synchronous detection can be used as a means of discriminating between photoelectrochemical signals and nonphotoelectrochemical signals. For example, a modulated light source resulting in a modulated signal can be detected with a lock-in amplifier.

The present invention also provides a kit for assaying analytes. In one embodiment, the kit comprises: a) a reactant capable of binding and/or reacting with an analyte under suitable conditions to allow binding of the analyte, if present in a sample, to the reactant; and b) a means for assessing binding and/or reacting between the analyte and the reactant to determine presence and/or amount of the analyte in the sample. The reactant, analyte, or additional reactant or additional analyte or analyte analog is labeled with a photoelectrochemically active molecule. The means for assessing the binding and/or reacting between the analyte and the reactant further comprises a means for converting the photoelectrochemically active molecule with light to an excited state in the presence of an electrode, and a means for assessing an electric current generated by an electron transfer between the excited photoelectrochemically active molecule and the electrode.

Preferably, the reactant and analyte or analyte analog are members of a specific binding pair. Any specific binding pairs known in the art, as previously described above, can be used in the kit. Any photoelectrochemically active labels known in the art, as previously described above, can be used in the kit. Any means known in the art for assessing an electric current generated by an electron transfer from the excited photoelectrochemically active molecule to the electrode can be used in the kit.

D. EXAMPLES

Example I

Preparation of Nanocrystalline Titanium Dioxide Paste

Tetrabutyl titanate was added dropwise into pH 1 water (adjusted with nitric acid) while stirring to obtain a yellow solution. The solution was stirred further after all tetrabutyl titanate was added. Its temperature was raised to 80° C. and kept constant. The solution changed to milk white. 50 mL of the solution was taken out, put into a quartz beaker, and autoclaved at 230° C. for 12 h. The titanium dioxide ($TiO_2$) nanoparticles produced above were dispersed by ultrasonication, and mixed with 40% carbon wax for 24 h to obtain $TiO_2$ paste.

Example II

Preparation of Ruthenium Poly-Pyridine Adsorbed Titanium Dioxide Electrode

A layer of $TiO_2$ was spread on an ITO conducting glass by the doctor blade technique. After drying, the film was heated in air at 450° C. for 30 min, and then cooled to 80° C. The electrode was immediately immersed in a 1 mM solution of ruthenium poly-pyridine in absolute ethanol, and soaked for 10 h in dark. Excess ruthenium poly-pyridine was rinsed off with ethanol.

Example III

Photocurrent Measurement

Photocurrent was measured on a CHI 800 electrochemical analyzer using the time-based mode. The light source consisted of a 500 W Xe lamp and a monochromator. The rectangular photoelectrochemical cell was made of polished glass, and had a Pt flag counter electrode, and a Ag/AgCl reference electrode. Light beam entered the cell perpendicular to the cell wall, and hit the $TiO_2$ electrode on its backside. Light was turned on and off by manually dialing the wavelength selector between the desired wavelength and 800 nm (where ruthenium poly-pyridine did not absorb light).

In FIG. 1, a $TiO_2$ film electrode adsorbed with ruthenium tris-(4,4'-dicarboxyl-2,2'-bipyridine) was placed in the photoelectrochemical cell containing 10 mM hydroquinone/phosphate buffer. Monochromator selector was dialed to 470 nm at every 20th second, and to 800 nm at every 40th second. The broken line is for the electrode adsorbed with ruthenium tris-(4,4'-dicarboxyl-2,2'-bipyridine), whereas the solid line is for the uncoated electrode.

Figure 2:
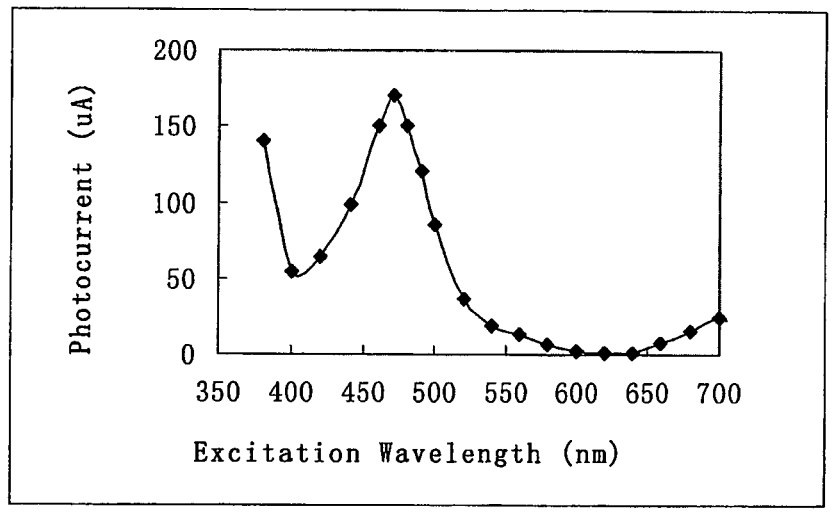
FIG. 2 illustrates an action spectrum of ruthenium tris(4,4'-dicarboxyl-2,2'-bipyridine) adsorbed on $TiO_2$ film electrode.

In FIG. 2, a $TiO_2$ film electrode adsorbed with ruthenium tris-(4,4'-dicarboxyl-2,2'-bipyridine) was placed in the photoelectrochemical cell containing 10 mM hydroquinone/phosphate buffer. Monochromator selector was dialed to a wavelength between 700 nm and 380 nm, and the corresponding photocurrent was measured. The action spectrum thus obtained looks similar to the absorption spectrum of ruthenium tris(4,4'-dicarboxyl-2,2'-bipyridine), indicating the photocurrent was generated by the metal complex.

Example IV

Preparation of Biotin Labeled Bovine Serum Albumin (BT-BSA)

4.9 mg of biotin-NHS was dissolved in 0.25 mL DMSO, and added dropwise into 5 mL of 2.5% bovine serum albumin (BSA) in 100 mM sodium phosphate, pH 7.5. The solution was stirred for 2 h at room temperature. Unreacted biotin-NHS was removed by centrifugation using a 10K cutoff tube. BSA concentration was determined from its absorbance at 280 nm.

Example V

Preparation of Ruthenium Complex Labeled Avidin (Ru-Avidin)

N-hydroxysuccinimide (23 mg) and 1-ethyl-3-(3-dimethylaminopropyl)carbodiimide (156 mg) were dissolved in anhydrous DMF, and stirred for 2 min in an ice bath. Ruthenium bis(2,2'-bipyridine)(4,4'-dicarboxyl-2,2'-bipyridine) (9 mg) was added, and mixed for 5 h in the ice bath. 0.5 mL of the activated ruthenium complex was added to 10 mg avidin in 5.3 mL PBS (pH 7.95). The solution was stirred gently at room temperature for 1 h. Small molecules were removed from the labeled protein by ultracentrifugation using a 10K cutoff tube. The labeling ratio was determined by UV-Vis absorbance.

Example VI

Detection of Biotin-Avidin Binding by Photoelectrochemistry (I)

Figure 3:
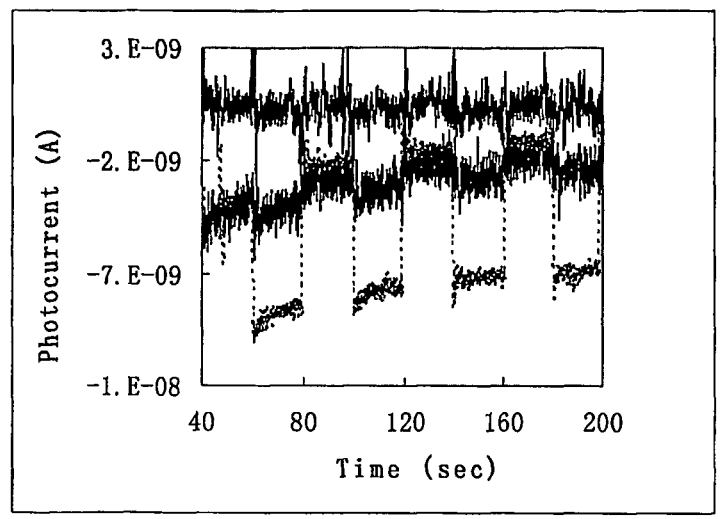
FIG. 3 illustrates photocurrent response of biotin-BSA coated $TiO_2$ electrode (black); biotin-BSA coated electrode in contact with labeled avidin (red); and BSA coated electrode in contact with labeled avidin (green).

$TiO_2$ electrodes were coated with biotin-BSA or BSA by immersing in the protein solution (1.4 mg/mL, pH 5.4) for 2 h at room temperature. One electrode coated with BSA (no biotin) was placed in the photoelectrochemistry cell, and the photocurrent was measured following the procedure described in Example III. This measurement provided background photocurrent. Other electrodes coated with biotin-BSA or BSA were then incubated in a Ru-avidin solution (1 uM, 0.1M phosphate buffer, pH 7.5) for 1 h at room temperature. After rinsing with phosphate buffer, the electrodes were used for photocurrent measurement, as described above. The electrodes coated with BSA provided photocurrent from Ru-avidin non-specifically bound to the electrodes, whereas the electrodes coated with biotin-BSA provided current from both specifically and non-specifically bound Ru-avidin. The specific signal (the broken line in FIG. 3) was approximately six times higher than the non-specific signal.

Example VII

Preparation of BSA Labeled with Both Biotin and Ruthenium Compound (BT-BSA-Ru)

N-hydroxysuccinimide (23 mg) and 1-ethyl-3-(3-dimethylaminopropyl) carbodiimide (156 mg) were dissolved in anhydrous DMF, and stirred for 2 min in an ice bath. Ruthenium bis(2,2'-bipyridine)(4,4'-dicarboxyl-2,2'-bipyridine) (9 mg) was added, and mixed for 5 h in the ice bath. 0.5 mL of the activated ruthenium complex was added to 10 mg BSA in 5.3 mL PBS (pH 7.95). The solution was stirred gently at room temperature for 1 h. 4.9 mg of biotin-NHS was dissolved in 0.25 mL DMSO, and added dropwise into the above BSA solution. The solution was mixed for 1 h at room temperature. Small molecules were removed from the labeled protein by ultracentrifugation using a 10K cutoff tube. The labeling ratio was determined by UV-Vis absorbance Example VIII Detection of Biotin-Avidin Binding by Photoelectrochemistry (II)

$TiO_2$ electrodes were coated with avidin or BSA by immersing in the protein solution (0.5 mg/ml, 20 mM phosphate, pH=7.5) for half hour at room temperature. One electrode coated with avidin was placed in the photoelectrochemistry cell, and the photocurrent was measured following the procedure described in Example III. This measurement provided background photocurrent.

Other electrodes coated with avidin or BSA were then incubated with a series of BT-BSA-Ru solutions (0.1 mg/ml; 0.03 mg/ml; 0.01 mg/ml; 0.003 mg/ml; 0.001 mg/ml, all in 20 mM phosphate buffer, pH=7.5) for one hour at room temperature. After rinsing with the phosphate buffer containing 0.1% Tween, the electrodes were used for photocurrent measurement, as described above.

The electrodes first coated with BSA provided photocurrent for BT-BSA-Ru non-specifically bound to the electrodes, whereas the electrodes first coated with avidin provided photocurrent for both specifically and non-specifically bound BT-BSA-Ru.

Figure 4:
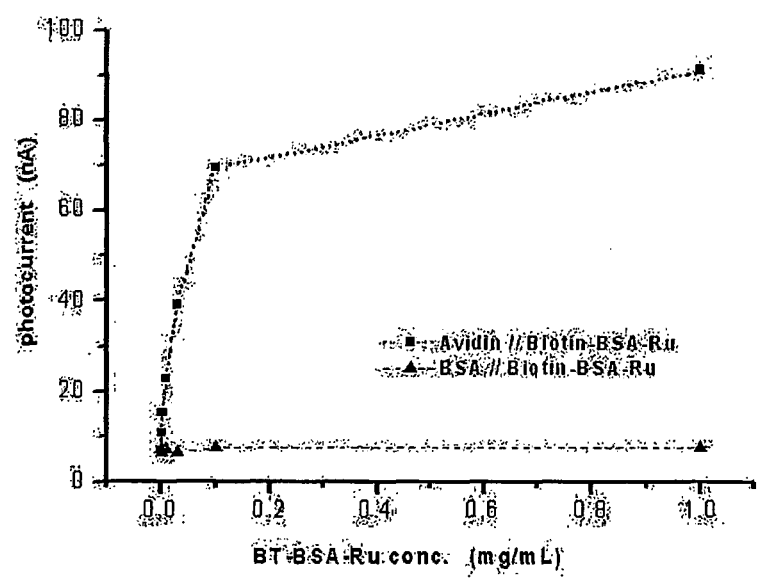
FIG. 4 illustrates photocurrent response of a series of concentrations of BSA dual-labeled with biotin and ruthenium compound after contact with BSA-coated $TiO_2$ electrode (triangle dots); and avidin coated electrode (square dots).
Figure 5:
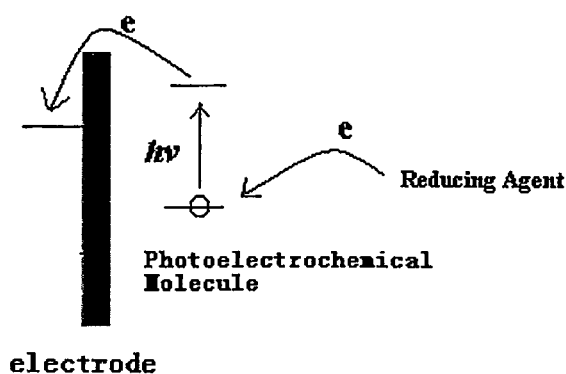
FIG. 5 illustrates a photoelectrochemical reaction.

Signal for non-specifically bound BT-BSA-Ru did not change much with the protein concentration, whereas the signal for the specifically bound BT-BSA-Ru initially increased linearly with the protein concentration, then leveled off at higher protein concentrations (FIG. 4).

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for assaying an analyte, which method comprises:
   a) contacting a sample suspected of containing an analyte with a reactant labeled with a photoelectrochemically active molecule and capable of binding and/or reacting with said analyte under suitable conditions to allow binding of said analyte, if present in said sample, to said reactant;
   b) converting said photoelectrochemically active molecule with light to an excited state in the presence of an electrode having an energy level that is lower than the energy level of said excited state and a reducing agent incapable of receiving an electron from said excited state photoelectrochemically active molecule, to generate an electron transfer from said excited state photoelectrochemically active molecule to said electrode, thereby producing an oxidized photoelectrochemically active molecule at a ground state;
   c) converting said oxidized photoelectrochemically active molecule at a ground state by said reducing agent to a reduced photoelectrochemically active molecule at a ground state that can be again excited with light;
   d) repeating steps b) and c); and
   e) assessing an electric current generated by said electron transfer from said excited photoelectrochemically active molecule to said electrode to determine presence and/or amount of said analyte in said sample.

2. The method of claim 1, wherein the analyte is selected from the group consisting of a cell, a cellular organelle, a virus, and a molecule.

3. The method of claim 2, wherein the cell is selected from the group consisting of an animal cell, a plant cell, a fungus cell, a bacterium cell, a recombinant cell and a cultured cell.

4. The method of claim 2, wherein the cellular organelle is selected from the group consisting of a nuclei, a mitochondrion, a chloroplast, a ribosome, an ER, a Golgi apparatus, a lysosome, a proteasome, a secretory vesicle, a vacuole and a microsome.

5. The method of claim 2, wherein the molecule is selected from the group consisting of an inorganic molecule, and an organic molecule.

6. The method of claim 5, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, and a lipid.

7. The method of claim 1, wherein the analyte is selected from the group consisting of a hormone, a cancer marker, a steroid, a sterol, a pharmaceutical compound, a metabolite of a pharmaceutical compound and a complex thereof.

8. The method of claim 1, wherein the sample is a mammalian sample.

9. The method of claim 8, wherein the mammal is selected from the group consisting of bovine, goat, sheep, equine, rabbit, guinea pig, murine, human, feline, monkey, dog and porcine.

10. The method of claim 1, wherein the sample is a clinical sample.

11. The method of claim 10, wherein the clinical sample is selected from the group consisting of serum, plasma, whole blood, sputum, cerebral spinal fluid, amniotic fluid, urine, gastrointestinal contents, hair, saliva, sweat, gum scrapings and tissue from biopsies.

12. The method of claim 10, wherein the clinical sample is a human clinical sample.

13. The method of claim 1, wherein the sample is a body fluid sample.

14. The method of claim 1, wherein the reactant binds and/or reacts specifically with the analyte.

15. The method of claim 1, wherein the reactant is selected from the group consisting of a cell, a cellular organelle, a virus, a molecule and an aggregate or complex thereof.

16. The method of claim 1, wherein the reactant is an antibody.

17. The method of claim 1, wherein the reactant is a nucleic acid.

18. The method of claim 1, wherein the photoelectrochemically active molecule is a metal polypyridyl complex.

19. The method of claim 1, wherein the photoelectrochemically active molecule has the formula,

wherein M is a metal ion, $L_1$, $L_2$, $L_3$ are mono-dentate ligands of M, $P_1$, $P_2$, $P_3$ are poly-dentate ligands of M, R is a spacer, X is a reactive chemical group capable of linking the photoelectrochemically active molecule to a reactant or an analyte, m, n, o, p and q are either zero or a positive integer, and total number of bonds provided by all the ligands equal to the coordination number of M.

20. The method of claim 19, wherein the M is selected from the group consisting of osmium, ruthenium, zinc, magnesium and aluminum.

21. The method of claim 19, wherein the $L_1$, $L_2$ or $L_3$ is a cyanide or a thiocyanide.

22. The method of claim 19, wherein the $L_1$, $L_2$, $L_3$ are the same or different.

23. The method of claim 19, wherein the $P_1$, $P_2$ or $P_3$ is a nitrogen-containing aromatic heterocycle.

24. The method of claim 23, wherein the nitrogen-containing aromatic heterocycle is selected from the group consisting of bipyridyl, bipyrazyl, terpyridyl, phenanthrolyl and phthalocyanine.

25. The method of claim 24, wherein the bipyridyl, bipyrazyl, terpyridyl and phenanthrolyl are unsubstituted or substituted.

26. The method of claim 25, wherein the substituted group is selected from the group consisting of an alkyl, an aryl, an aralkyl, a carboxylate, a carboxyaldehyde, a carboxamide, a cyano, an amino, a hydroxycarbonyl, a hydroxyamino, an aminocarbonyl, an amidine, a guanidium, a ureide, a sulfur-containing group, a phosphorous-containing group and a carboxylate ester of N-hydroxysuccinimide.

27. The method of claim 19, wherein the R is a $C_2$ to $C_{12}$ alkyl or poly(ethylene glycol).

28. The method of claim 19, wherein the R is a poly(ethylene glycol).

29. The method of claim 19, wherein the X is selected from the group consisting of a N-hydroxysuccinimide ester, a sulfhydryl, an epoxide, an aldehyde, a maleic anhydride, an imidoester, an amino, a carboxyl, an isothiocyanate, a maleimide, a haloacetyl, a hydrazide and a phosphoramidite.

30. The method of claim 1, wherein the reactant or the analyte is labeled with a photoelectrochemically active molecule.

31. The method of claim 1, which is conducted in a competition assay format wherein the reactant and the analyte from the sample are not labeled and a separate analyte or analyte analog labeled with a photoelectrochemically active molecule is used.

32. The method of claim 1, which is conducted in a sandwich assay format wherein a first reactant and the analyte from the sample are not labeled and a second reactant labeled with a photoelectrochemically active molecule is used.

33. The method of claim 1, wherein the binding or reacting between the analyte and the reactant is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, chemiluminescence assay, lateral flow immunoassay, μ-capture assay, inhibition assay, energy transfer assay, avidity assay, turbidometric immunoassay and time resolved amplified cryptate emission (TRACE) assay.

34. The method of claim 1, wherein the reducing agent is a hydroquinone.

* * * * *

UNITED STATES PATENT AND TRADEMARK OFFICE
CERTIFICATE OF CORRECTION

PATENT NO.         : 8,603,750 B2                                      Page 1 of 1
APPLICATION NO.    : 10/535905
DATED              : December 10, 2013
INVENTOR(S)        : Guo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1840 days.

Signed and Sealed this
Twenty-third Day of May, 2017

Michelle K. Lee
*Director of the United States Patent and Trademark Office*